United States Patent [19]

Narita et al.

[11] Patent Number: 5,124,474

[45] Date of Patent: Jun. 23, 1992

[54] PROCESS FOR COMMERICAL-SCALE CRYSTALLIZATION AND PURIFICATION OF TETRAKIS[3-(3,5-DI-TERT-BUTYL-4-HYDROXYPHENYL)PROPIONYL-OXYMETHYL]METHANE FOR STABLY OBTAINING BETA CRYSTALS THEREOF

[75] Inventors: Noritsugu Narita; Makoto Maruno, both of Mie, Japan

[73] Assignee: Yoshitomi Pharmaceutical Industries, Ltd., Osaka, Japan

[21] Appl. No.: 445,646

[22] PCT Filed: Mar. 29, 1989

[86] PCT No.: PCT/JP89/00333

§ 371 Date: Nov. 29, 1989

§ 102(e) Date: Nov. 29, 1989

[87] PCT Pub. No.: WO89/09202

PCT Pub. Date: Oct. 5, 1989

[30] Foreign Application Priority Data

Mar. 31, 1988 [JP] Japan ................................. 63-84907
May 27, 1988 [JP] Japan ................................. 63-130693

[51] Int. Cl.⁵ .............................................. C07C 69/76
[52] U.S. Cl. ....................................................... 560/75
[58] Field of Search ............................................ 860/75

[56] References Cited

U.S. PATENT DOCUMENTS 4,739,102 4/1988 Tokunaga ............................ 560/75

Primary Examiner—Paul J. Killos
Attorney, Agent, or Firm—Wenderoth, Lind & Ponack

[57] ABSTRACT

A process for the commercial-scale crystallization and purification of tetrakis[3-(3,5-di-tert-butyl-4-hydroxyphenyl)propionyloxymethyl]methane which comprises melt-blending the reaction mixture resulting from the transesterification between pentaerythritol and a lower alkyl 3-(3,5-di-tert-butyl-4-hydroxyphenyl)propionate and containing tetrakis[3-(3,5-di-tert-butyl-4-hydroxyphenyl)propionyloxymethyl]methane with a water-soluble solvent under reflux, then blending the resulting melt-blend with a cooled, mixed solvent composed of 0.2–1.5 parts by weight, per part by weight of the above-mentioned reaction mixture, of a water-soluble solvent and 0.06–0.09 part by weight, per part by weight of the water-soluble solvent, of water to thereby cause crystallization, and further adding water for stabilizing the resulting beta crystal structure.

The process according to the invention can produce the above-mentioned compound in the beta crystal form, namely as white crystals having an excellent color feature and a purity quite satisfactory from the practical viewpoint, without encountering scaling on the apparatus or troubles in the operational procedure, for example, loss of stirrability due to fine powder formation.

6 Claims, 6 Drawing Sheets

PROCESS FOR COMMERICAL-SCALE CRYSTALLIZATION AND PURIFICATION OF TETRAKIS[3-(3,5-DI-TERT-BUTYL-4-HYDROXY-PHENYL)PROPIONYL-OXYMETHYL]METHANE FOR STABLY OBTAINING BETA CRYSTALS THEREOF

TECHNICAL FIELD

The present invention relates to a process for the crystallization and purification of tetrakis[3-(3,5-di-tert-butyl-hydroxyphenyl)propionyloxy-methyl]methane, which is useful as an antioxidant for polyolefins and other materials for stably obtaining beta crystals thereof on a commercial scale.

BACKGROUND ART

It is known from U. S. Pat. No. 3,644,482 that tetrakis[3-(3,5-di-tert-butyl-4-hydroxyphenyl)propionyloxymethyl]methane(hereinafter sometimes referred to as "compound I") can be produced by transesterification between a lower alkyl 3-(3,5-di-tert-butyl-4-hydroxyphenyl)propionate and pentaerythritol in the presence of a base catalyst, such as an alkali metal lower alkoxide.

Recent investigations into the crystal structure of compound I have revealed that compound I can occur in at least four crystal forms, namely alpha, beta, gamma and delta (U.S. Pat. No. 4,405,807). Among them, alpha crystals, when crystallization is carried out in the conventional manner, tend to become a fine powder, making stirring impossible, as described in the above-cited U.S. patent. As a result, crystals obtained have poor purity and color features. Therefore, from the production process and product handling viewpoints, among others, the beta crystal structure is a suitable one. For the production of beta crystals, a process is known from Laid-open European Patent Specification No. 244,361 which comprises dissolving the transesterification product in a water-soluble solvent, such as methanol or ethanol, which contains 2-10% by weight of water and, after clarifying and filtering as necessary, cooling the solution for gradual temperature fall. When the crystallization liquor is cooled gradually, however, the crystal structure changes in part to the alpha structure, which is unfavorable from the product handling viewpoint, as mentioned above. In addition, when the slurry obtained after crystallization is maintained under stirring, the crystal structure change from beta to alpha progresses with the lapse of time. Thus, it is very difficult to produce beta crystals on a commercial scale in a well-reproducible and stable manner by the crystallization process described in the above-cited laid-open European patent specification. When beta crystals are stored in a wet state at room temperature, the crystal structure changes to alpha. In view of this fact as well, it is very difficult to produce beta crystals stably on a commercial scale.

It is an object of the invention to provide an industrially advantageous process for obtaining beta crystals of compound I in a stable manner.

DISCLOSURE OF THE INVENTION

As a result of intensive investigations made in an attempt to solve the problems mentioned above and produce beta crystals stably on a commercial scale, the present inventors found that the object of the invention can be accomplished by following a crystallization/purification process which comprises first melt-blending compound I with a solvent under reflux and then pouring the blend into a cooled specific solvent to thereby attain rapid cooling and they have now completed the present invention. The invention thus relates to a process for the crystallization and purification of tetrakis[3-(3,5-di-tert-butyl-4-hydroxyphenyl)propionyloxymethyl]methane which comprises melt-blending the reaction mixture resulting from the transesterification between pentaerythritol and a lower alkyl 3-(3,5-di-tert-butyl-4-hydroxyphenyl)propionate and containing tetrakis[3-(3,5-ditert-butyl-4-hydroxyphenyl)propionyloxymethyl]methane with a water-soluble solvent under reflux, then blending the resulting melt-blend with a cooled, mixed solvent compound of 0.2-1.5 parts by weight, per part by weight of said reaction mixture, of a water-soluble solvent and 0.06-0.09 part by weight, per part by weight of said water-soluble solvent, of water to thereby cause crystallization and further adding water for stabilizing the resulting beta crystal structure.

The compound I-containing reaction mixture to be used in the practice of the invention may be the transesterification reaction mixture itself or the residue (syrupy in most cases) remaining after concentration for removal of the solvent used in the step of catalyst removal for the purpose of fluidity improvement.

In accordance with the invention, compound I exclusively having the beta crystal structure can be obtained by meltblending such transesterification reaction mixture, or the residue after concentration for removal of the solvent used in the step of catalyst removal for the purpose of fluidity improvement, with a water-soluble solvent (e.g. methanol, ethanol, mixture of these, etc.) added thereto, under reflux, pouring the melt-blend into and blending the same with a cooled solvent composed of a water-soluble solvent (e.g. methanol, ethanol, mixture of these, etc.) and water and containing, as necessary, beta-structure seed crystals preferably in an amount of 0.01-1% by weight based on the transesterification reaction product, to thereby cause crystallization, further adding water for the stabilization of the beta crystals formed, and isolating the resulting crystals, followed, as necessary, by washing and drying.

In the step of melt-blending, the aqueous solvent is used in an amount of 0.1-1 part by weight, preferably 0.4-0.6 part by weight, per part by weight of the reaction product containing compound I. The blending may be started at a temperature at which the reaction product containing compound I can be melted in the aqueous solvent, generally at 100°-150° C., preferably 120°-130° C. The solution resulting from the blending is maintained at the refluxing temperature of the solvent. The maintenance period should not be very longer than a period sufficient for dissolution; it should be not longer than 2 hours. A longer maintenance period may allow precipitation of a trace amount of alpha crystals, which might serve as seed crystals in the step of pouring the solution into the cooled solvent and cause contamination of the product with alpha crystals. The recrystallization solvent to be used, namely the solvent composed of a water-solvent and water, is preferably composed of 0.2-1.5 parts by weight, per part by weight of the reaction product containing compound I, of said water-soluble solvent and 0.06-0.09 part by weight, per part by weight of said water-soluble solvent, of water and should be cooled to and maintained generally, at 0°-30° C., preferably 15°-25° C. The liquid obtained in the above manner by melt-blending in the water-soluble solvent under reflux is poured into and mixed with said recrystallization solvent for attaining a temperature of 10°-50° C., preferably 35°-45° C., whereby crystals precipitate out. By further adding water to the thus-obtained crystallization mixture containing beta crystals, beta crystals of compound I can be obtained stable on a commercial scale without causing any subsequent change in crystal structure. The addition of water has not only the advantage of contributing to increased stabilization of the beta crystal structure but also the advantage of increasing the crystallization yield because of the resulting decrease in solubility as compared with the solubility of the solvent itself. A further advantageous feature is that the admixing with water results in an improvement in safety from combustion or explosion; this feature is favorable from the industrial viewpoint. The amount of water to be admixed is generally no more than 0.2 part by weight, preferably 0.1-0.2 part by weight, per part by weight of the water-soluble solvent used. When the amount of water exceeds 0.2 part by weight, such quality features of the product as purity and color tend to become markedly inferior. The addition of water may be performed at a time or continuously or intermittently.

The granular compound I obtained by the method of the invention occurs as white granules showing a high bulk specific gravity, high flowability and other favorable properties. When analyzed by differential scanning calorimetry (DSC), by which a change in crystal structure can be known more definitely than X ray diffraction spectrometry since alpha crystals show an endothermic melting peak center at 121°-123° C. and beta crystals at 113°-115° C., it shows a single endothermic peak having its center at 113°-115° C. In X ray (Cu-Kα) diffractometry, it gives five peaks within the 2θ (diffraction angle) range of 5°-10.6°, which are characteristic of beta crystals, as described in U.S. Pat. No. 4,405,807. Based on these and other facts, it can be concluded that said compound has the beta crystal structure alone. The beta crystals obtained can keep their crystal structure stably. In the prior art processes, it is difficult to produce beta crystals of compound I on a commercial scale since compound I is readily discolored or the beta crystal structure changes to the alpha crystal structure. On the contrary, the process according to the invention makes it possible to produce the compound in the form of beta crystals readily and stably on a commercial scale without causing troubles in operational procedure, for example, scaling of the apparatus and loss of stirrability due to fine powder formation. The product beat crystals occur as white crystals which are good in color and are quite satisfactory in purity from the practical viewpoint.

EXAMPLES

The following reference examples, working examples and comparative examples are further illustrative of the invention but are by no means limitative of the scope thereof.

Reference Example 1

A four-necked flask fitted with stirrer, condenser, thermometer and nitrogen inlet tube was charged with 182.7 g (0.625 mole) of methyl 3-(3,5-di-tert-butyl-4-hydroxyphenyl)propionate, 18.9 g (0.139 mole) of pentaerythritol and 0.73 g (0.0035 mole) of monobutyltin oxide, the temperature was raised to 185° C. and the reaction was carried out for 1 hour while the byproduct methanol was distilled off. Then, nitrogen gas (2 NL/HV) was bubbled into the liquid reaction mixture under reduced pressure (60-70 mm Hg). After 18 hours of bubbling, the reaction was completed. [The content of the tri-substituted compound (A) not yet fully esterified in the mixture at the time of completion of the reaction was not more than 5% (HPLC (S/S)]. The excess methyl 3-(3,5-di-tert-butyl-4-hydroxyphenyl)-propionate was distilled off over 1 hour in the manner of thin film distillation at 150°-185° C. and 0.5-0.2 mm Hg. The distillate weighed 19.5 g, the percent recovery being 97%. This distillate can be used as it is in the next reaction batch.

The remaining reaction mixture was cooled to 115° C., the pressure was returned to atmoshperic pressure by nitrogen gas introduction, and the mixture was uniformly dissolved in toluene.

The toluene solution was washed with 400 g (0.16 mole) of 5% aqueous oxalic acid solution and then, at 60° C., with two 40-g portions of water. The toluene layer was concentrated at 125° C. and 30 mm Hg for 1 hour to give a light-yellow syrup of tetrakis[3-(3,5-di-tert-butyl-4-hydroxyphenyl)propionyloxymethyl]methane.

EXAMPLE 1

Figure 1:
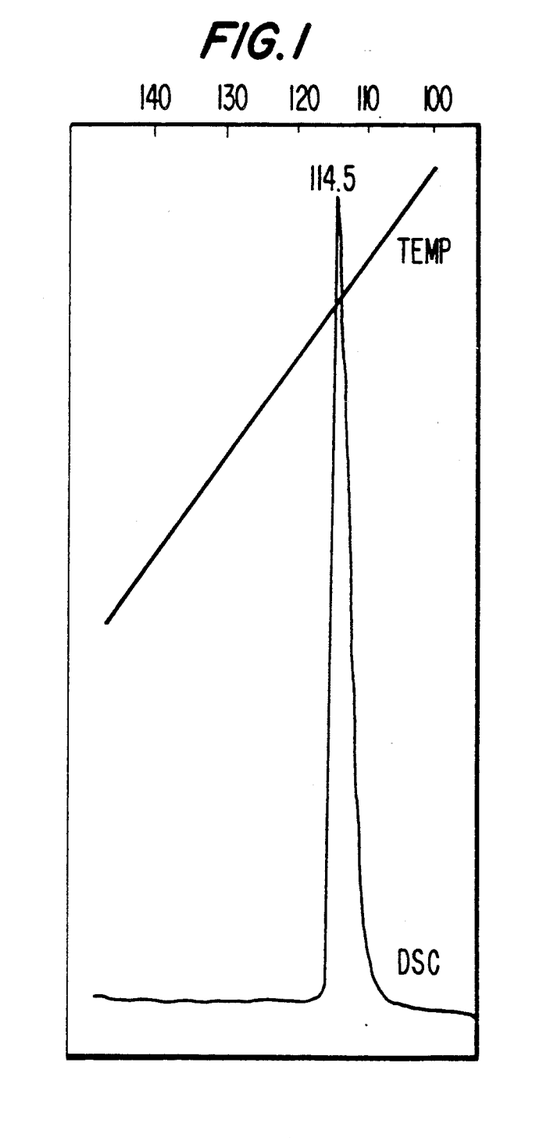
FIG. 1 and FIG. 2 show an analytical pattern in differential scanning calorimetry and an X ray (Cu-Kα) diffraction spectrum, respectively, of the product of Example 1.
Figure 2:
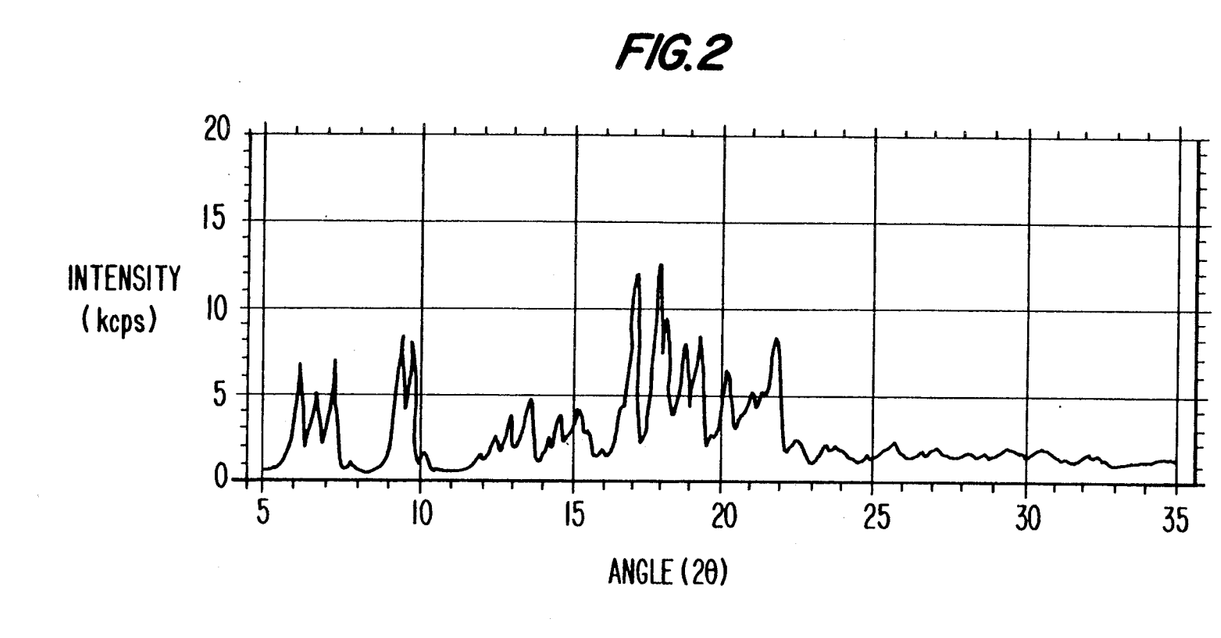

Methanol (50 g) was added portionwise to 100 g of the syrup obtained in Reference Example 1 (the initial temperature of the syrup being 125° C.) and melt-blending was caused to occur under reflux (68° C.). The melt-blend was poured into a cooled (20°-25° C.) and stirred recrystallization solvent composed of 92.5 g of methanol and 7.5 g of water and containing seed crystals (0.1 g) added thereto, whereupon the inside temperature became 42° C. Then, crystals are allowed to precipitate out with stirring for 1 hour while the inside temperature was maintained at 35°-45° C. Water (17.6 g) was then added and the resulting mixture was stirred for 1 hour, then cooled to 20° C. and maintained at that temperature for 48 hours with stirring. The precipitate was collected by centrifugation and dried, whereby 83 g of white granular crystals were obtained with a bulk specific gravity of 0.57. DSC analysis of this compound have a single endothermic melting peak with the peak center at 114.5° C. This supports that the crystals are exclusively beta crystals (FIG. 1). That the crystals have the beta crystal structure was also confirmed by X ray (Cu-Kα) diffraction spectrometry (FIG. 2). The melting point determined on a melting point measuring apparatus equipped with a microscope was 111°-115°

C. and the crystal purity determined by liquid chromatography was not less than 98%.

EXAMPLE 2

The procedure of Example 1 was followed in the same manner using 50 g of the syrup obtained in Reference Example 1 except that ethanol was used as the solvent and that the quantities of the solvent and water were each reduced to half as compared with Example 1. Granular crystals were obtained. They weighed 41 g and had a bulk specific gravity of 0.52. DSC analysis of this compound showed a single endothermic peak with the peak center at 114° C. This supports that the crystals are exclusively of the beta crystal structure. That the crystals have the beta crystal structure was also confirmed by X-ray (Cu-K$\alpha$) diffraction spectrometry. The melting point was 112°-115° C. and the crystal purity determined by liquid chromatography was not less than 98%.

EXAMPLE 3

A one-liter four-necked flask fitted with stirrer, condenser, thermometer and nitrogen gas inlet tube was charged with 671.6 g (2.3 moles) of methyl 3-(3,5-di-tert-butyl-4-hydroxyphenyl)propionate, 68.0 g (0.50 mole) of pentaerythritol, 2.25 g (10.9 millimoles) of monobutyltin oxide, 0.16 g (0.57 millimole) of monobutyltin trichloride (the total catalyst amount corresponding to 0.5 mole percent of the methyl propionate compound) and 100 g of toluene, and the reaction was carried out at 170°-175° C. with stirring for 12 hours. During the reaction period, 500 g of toluene was added dropwise and distilled off azetropically with the byproduct methanol. After completion of the reaction, 200 g of toluene was added for dissolution of the reaction mixture, then 200 g of 5% (by weight) aqueous oxalic acid solution was added, and the resultant mixture was stirred for 1 hour and then allowed to stand. The aqueous layer was removed and the organic layer was washed with two 200-g portions of water. The toluene was distilled off under reduced pressure to give 590 g of a syrupy substance containing tetrakis[3-(3,5-di-tert-butyl-4-hydroxyphenyl)propionyloxymethyl]methane.

A 100-g portion of this syrupy substance was treated following the procedure of Example 1 to give 81 g of white granular crystals having a bulk specific gravity of 0.55. Upon DSC analysis, this compound gave a single endothermic melting peak with its center at 114° C. This supports that the crystals are exclusively beta crystals. That the crystals have the beta crystal structure was also confirmed by X ray (Cu-K$\alpha$) diffractometry. The melting point was 110°-114° C. and the crystal purity (determined by liquid chromatography) was not less than 98%.

The bulk specific gravities and angles of repose of the beta crystals of tetrakis[3-(3,5-di-tert-butyl-4-hydroxyphenyl)propionyloxymethyl]methane as obtained in Example 1, Example 2 and Example 3 are summarized below in Table 1 in comparison with those of a typical commercial product.

TABLE 1

| | Example 1 | Example 2 | Example 3 | Commercial product |
|---|---|---|---|---|
| Bulk specific gravity | 0.57 | 0.52 | 0.55 | 0.45 |
| Angle of repose | 37° | 44° | 41° | 48° |

From the above data, it is evident that the products obtained in accordance with the invention are superior in flowability to the commercial product.

COMPARATIVE EXAMPLE 1

Figure 3:
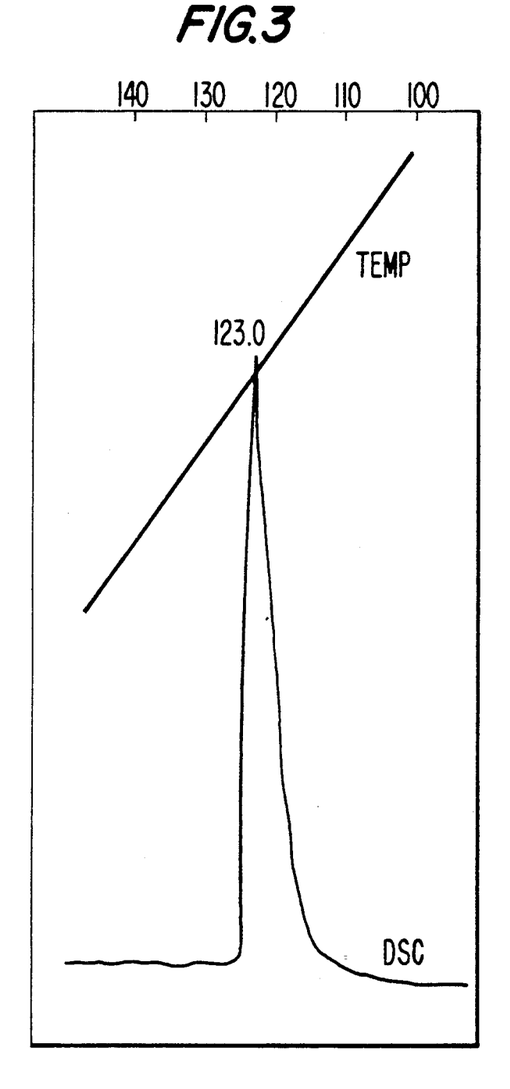
FIG. 3 and FIG. 4 show an analytical pattern in differential scanning calorimetry and an X ray (Cu-α) diffraction spectrum, respectively, of the product of Comparative Example 1.
Figure 4:
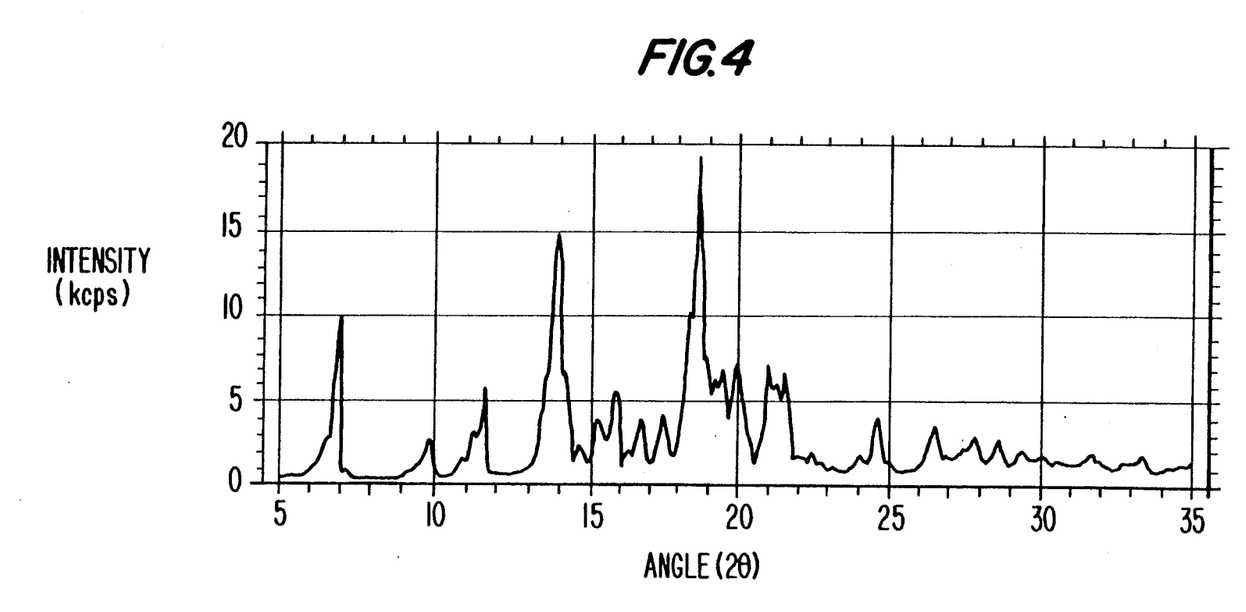

Methanol (25 g) was added portionwise to 50 g of the syrupy substance obtained in Reference Example 1 (the initial temperature of the syrup being 125° C.)and melt-blending was caused to occur under reflux (68° C.). The resultant melt-blend was poured into a cooled (20°-25° C.) and stirred recrystallization solvent composed of 46.3 g of methanol and 3.8 water and containing 0.1 g of seed crystals, whereupon the inside temperature became 43° C. Then the mixture was stirred at an inside temperature of 35°-45° C. for 1 hour for crystal precipitation, immediately followed by cooling to 20° C. After 4-5 hours of continued stirring, the crystals turned into a fine powder and stirring was no more possible. The crystals formed were collected by filtration using a glass filter, washed with methanol cooled to 20° C. and dried. The product showed a melting point of 121°-123° C. and, in DSC analysis, gave a peak (center at 123.0° C.) assignable to endothermic melting of alpha crystals (FIG. 3). It was confirmed by X ray (Cu-K$\alpha$) spectrometry that the crystals had the alpha crystal structure (FIG. 4).

COMPARATIVE EXAMPLE 2

A 1,000-ml four-necked flask fitted with stirrer, condenser for distillation, thermometer and toluene inlet tube was charged with 200 g (0.68 mole) or methyl 3-(3,5-di-tertbutyl-4-hydroxyphenyl)propionate, 21.2 g (0.15 mole) of pentaerythritol and 1 g of dibutyltin oxide, and the mixture was heated to 170° C. Toluene was added dropwise continuously for 12 hours while the byproduct methanol was distilled off. After driving the reaction to completion in this manner, the reaction mixture was diluted with toluene and the dibutyltin oxide was removed to give a toluene solution The toluene was distilled off to give 201 g of a light-yellow syrupy substance. A 100-g portion of the syrupy substance was treated in the same manner as in Comparative Example 1 for precipitation of crystals, immediately followed by cooling to 20° C. After 1 hour of continued stirring, the crystals turned into a fine powder, making stirring impossible. The crystals formed were collected by filtration using a glass filter, washed with cooled (20° C.) methanol and dried. They had a melting point of 121°-124.3° C. and, in DSC analysis, gave a peak (center at 123.2° C) due to endothermic melting of alpha crystals. By X ray (Cu-K$\alpha$) diffraction spectrometry, it was confirmed that they have the crystal structure of alpha crystals.

COMPARATIVE EXAMPLE 3

Methanol (71.3 g) was added portionwise to 50 g of the syrupy substance obtained in Reference Example 1 (the initial temperature of the syrup being 125° C.) and melt-blending was caused to occur under reflux (68° C.). Then, 3.8 g of water was added dropwise and the mixture was cooled gradually. When the inside temperature reached about 55° C., crystals began to precipitate out. Stirring was continued with cooling for 3 hours. The crystals produced were collected by filtration, washed with methanol and dried. When subjected to melting point determination, they melted at 11°–124° C. DSC analysis gave two endothermic melting peaks (peak center at 122.4° C., assignable to alpha crystals; peak center at 113.8° C., assignable to beta crystals). The alpha crystal to beta crystal quantity ratio was 28:72 as estimated on the area ratio.

COMPARATIVE EXAMPLE 4

Figure 5:
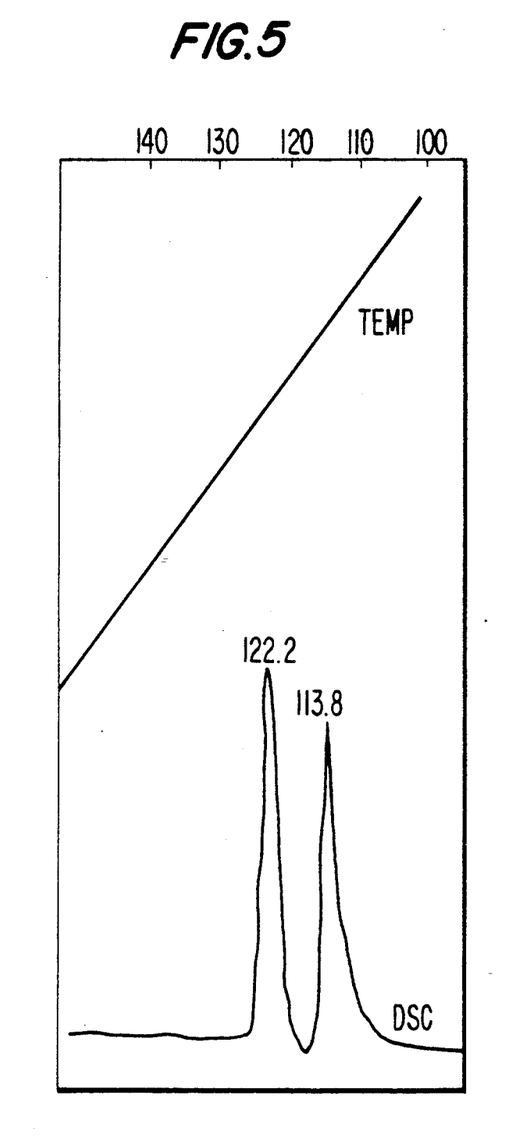
FIG. 5 and FIG. 6 show an analytical pattern in differential scanning calorimetry and an X ray (Cu-Kα) diffraction spectrum, respectively, of the product of Comparative Example 4.
Figure 6:
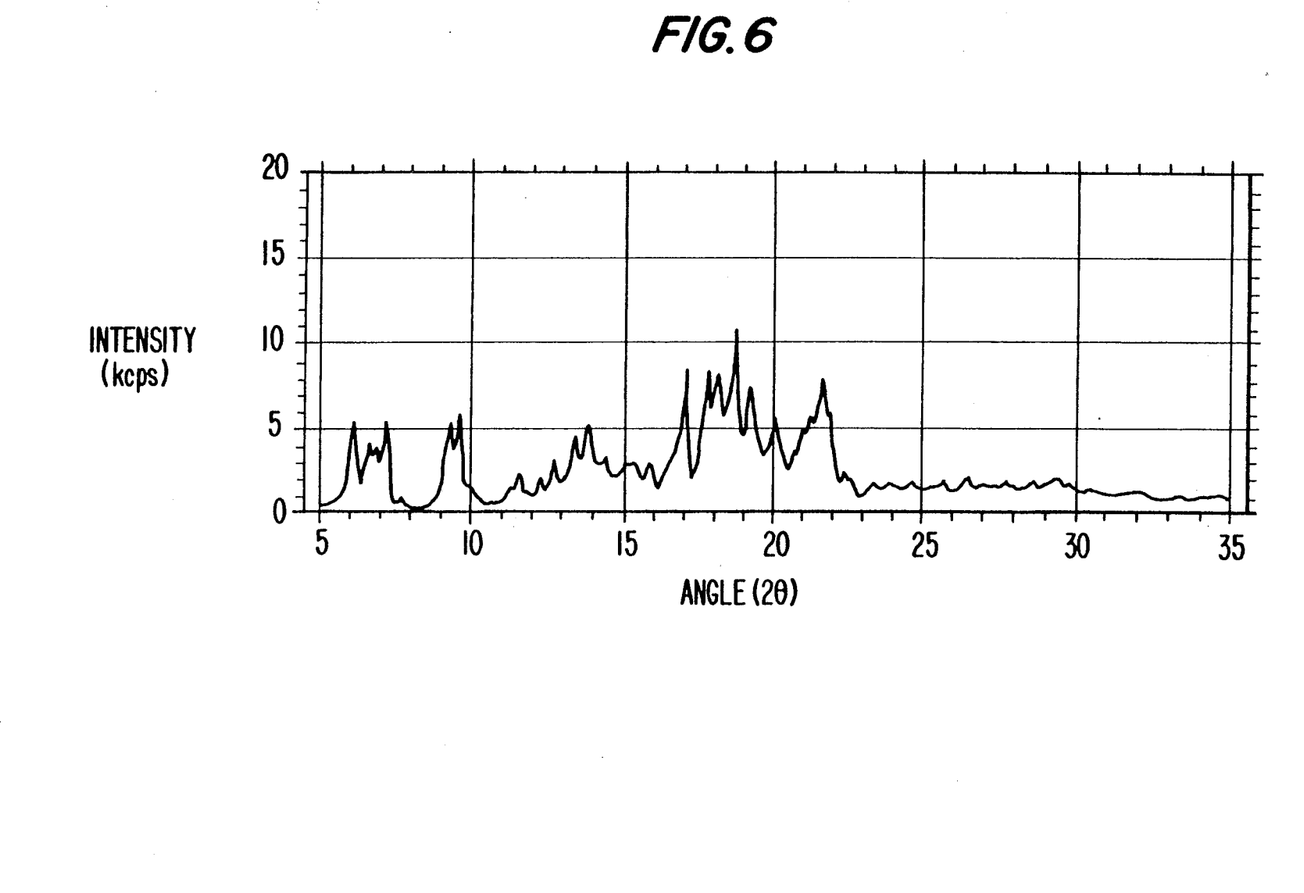

The procedure of Comparative Example 3 was followed in the same manner except that the period of stirring was extended from 3 hours to 5 hours. The crystal obtained showed a melting range of 111°–125° C. Their X ray (Cu-K$\alpha$) diffraction spectrum is shown in FIG. 6. In DSC analysis, they showed two endothermic melting peaks (peak center at 122.2° C., assignable to alpha crystals; peak center at 113.8° C., assignable to beta crystals) and the alpha crystal to beta crystal quantity ratio was estimated at 50:50 based on the area ratio (FIG. 5).

COMPARATIVE EXAMPLE 5

The procedure of Comparative Example 5 was followed in the same manner except that the period of stirring was extended from 3 hours to 10 hours. The crystals that had precipitated out turned into a fine powder, making stirring impossible. The crystals obtained showed a melting range of 121°–124° C. In DSC analysis, they showed a single endothermic melting peak (center at 122.8° C.); therefore, they the alpha crystal structure only. By X ray (Cu-K$\alpha$) diffractometry, it was confirmed that the compound had the alpha crystal structure.

COMPARATIVE EXAMPLE 6

A 50-g portion of the syrupy substance obtained in Example 3 was treated following the procedure of Comparative Example 5. The crystalline precipitate turned into a fine powder and stirring became impossible. The crystals formed were filtered off, washed with methanol and dried. They showed a melting range of 119°–123° C. and, in DSC analysis, they showed an endothermic melting peak (center at 122.5° C.) assignable to alpha crystals. By X ray (Cu-K$\alpha$) diffractometry, it was confirmed that the compound had the alpha crystal structure.

COMPARATIVE EXAMPLE 7

The procedure of Example 1 was followed in the same manner except that the step of melt-blending was conducted at a temperature (63°–65° C.) lower than the refluxing temperature (68° C.). The crystals obtained showed a melting range of 110°–125° C. In DSC analysis, they showed two endothermic melting peaks (center at 123.0° C., assignable to alpha crystals; center at 114.0° C., assignable to beta crystals). The alpha crystal to beta crystal quantity ratio as estimated from the area ratio was 20:80.

COMPARATIVE EXAMPLE 8

The procedure of Example 1 was followed in the same manner except that the melt-blend obtained by refluxing (68° C.) was maintained at that temperature for 4 hours. The crystals obtained showed a melting range of 111°–124° C. and, in DSC analysis, showed two endothermic melting peaks (center at 123.1° C., assignable to alpha crystals; center at 114.2° C., assignable to beta crystals). The alpha crystal to beta crystal quantity ratio as estimated from the area ratio was 35:65.

We claim:

1. A process for the crystallization and purification of tetrakis[3-(3,5-di-tert-butyl-4-hydroxyphenyl)propionyloxymethyl]methane which comprises melt-blending the reaction mixture resulting from the transesterification between pentaerythritol and a lower alkyl 3-(3,5-di-tert-butyl-4-hydroxyphenyl)propionate and containing tetrakis[3-(3,5-di-tertbutyl-4-hydroxyphenyl)propionyloxymethyl]methane with a water-soluble solvent under reflux, then blending the resulting melt-blend with a cooled, mixed solvent composed of 0.2–1.5 parts by weight, per part by weight of said reaction mixture, of a water-soluble solvent and 0.06–0.09 part by weight, per part by weight of said water-soluble solvent, of water to thereby cause crystallization, and further adding water for stabilizing the resulting beta crystal structure.

2. A process as claimed in claim 1, wherein the water-soluble solvent is used in an amount of 0.1–1 part by weight per part by weight of the reaction mixture.

3. A process as claimed in claim 1, wherein, in the step of melt-blending the reaction mixture containing tetrakis[3-(3,5-di-tert-butyl-4-hydroxyphenyl)propionyloxymethyl]methane with a water-soluble solvent under reflux, the resulting melt-blend is maintained at the refluxing temperature of the solvent used.

4. A process as claimed in claim 3, wherein the melt-blend is maintained at the refluxing temperature of the solvent used for a period of not more than 2 hours.

5. A process as claimed in claim 1, wherein the temperature arrived at upon blending the melt-blend with the cooled, mixed solvent is 10°–50° C.

6. A process as claimed in claim 1, wherein water is added in an amount of 0.1–0.2 part by weight per part by weight of the total of the water-soluble solvent(s) used.

* * * * *